United States Patent
Abe

(10) Patent No.: US 10,441,239 B2
(45) Date of Patent: Oct. 15, 2019

(54) X-RAY DIAGNOSTIC APPARATUS, AND METHOD OF ADJUSTING IRRADIATION RANGE OF X-RAY DIAGNOSTIC APPARATUS

(71) Applicant: Toshiba Medical Systems Corporation, Otawara-Shi (JP)

(72) Inventor: Shingo Abe, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 366 days.

(21) Appl. No.: 15/086,649

(22) Filed: Mar. 31, 2016

(65) Prior Publication Data

US 2016/0296195 A1 Oct. 13, 2016

(30) Foreign Application Priority Data

Apr. 9, 2015 (JP) .................................. 2015-080059

(51) Int. Cl.
*A61B 6/00* (2006.01)
*A61B 6/08* (2006.01)

(52) U.S. Cl.
CPC ................ *A61B 6/542* (2013.01); *A61B 6/08* (2013.01); *A61B 6/4441* (2013.01); *A61B 6/4464* (2013.01); *A61B 6/481* (2013.01); *A61B 6/504* (2013.01); *A61B 6/5217* (2013.01); *A61B 6/547* (2013.01)

(58) Field of Classification Search
CPC ......... A61B 6/542; A61B 6/4464; A61B 6/08; A61B 6/5217; A61B 6/4441; A61B 6/504; A61B 6/481; A61B 6/547

USPC .................................................. 600/407–430
See application file for complete search history.

(56) References Cited

U.S. PATENT DOCUMENTS

| | | | | |
|---|---|---|---|---|
| 2002/0151781 | A1* | 10/2002 | Ohishi | A61B 6/466 600/407 |
| 2002/0156368 | A1 | 10/2002 | Ohishi et al. | |
| 2003/0109779 | A1* | 6/2003 | Ohishi | A61B 6/466 600/407 |
| 2004/0066885 | A1* | 4/2004 | Ogawa | A61B 6/06 378/42 |
| 2004/0127789 | A1* | 7/2004 | Ogawa | A61B 6/481 600/425 |
| 2006/0082598 | A1* | 4/2006 | Ohishi | A61B 6/466 345/653 |

(Continued)

FOREIGN PATENT DOCUMENTS

| | | |
|---|---|---|
| JP | 2000-217035 | 8/2000 |
| JP | 2007-301228 | 11/2007 |

*Primary Examiner* — Sanjay Cattungal
(74) *Attorney, Agent, or Firm* — Oblon, McClelland, Maier & Neustadt, L.L.P.

(57) ABSTRACT

An X-ray diagnostic apparatus according to this embodiment includes: a memory circuitry configured to store a program; and a processing circuitry configured to read the program from the memory circuitry, and execute the program, wherein the processing circuitry is configured to identify a predetermined three-dimensional region of a patient at a predetermined position based on multiple X-ray images taken in at least two directions, and adjust an X-ray irradiation range based on the identified three-dimensional region and on system position information that includes irradiation position information where the patient is irradiated.

16 Claims, 8 Drawing Sheets

(56) References Cited

U.S. PATENT DOCUMENTS

2007/0092067 A1* 4/2007 Fujisawa ............... A61B 6/032
378/196
2011/0018871 A1* 1/2011 Shirahata ............... A61B 8/00
345/419

* cited by examiner

X-RAY DIAGNOSTIC APPARATUS, AND METHOD OF ADJUSTING IRRADIATION RANGE OF X-RAY DIAGNOSTIC APPARATUS

CROSS-REFERENCE TO RELATED APPLICATION

This application is based upon and claims the benefit of priority from Japanese Patent Application No. 2015-080059, filed on Apr. 9, 2015, the entire contents of which are incorporated herein by reference.

FIELD

The present invention relates to an X-ray diagnostic apparatus, and a method of adjusting the irradiation range of the X-ray diagnostic apparatus.

BACKGROUND

In recent years, coronary intervention has been being performed to treat myocardial infarction and angina pectoris. The coronary intervention is a method of performing treatment by, for example, forming a small hole at the base of a thigh, a wrist, an elbow or the like, inserting a thin tubular treatment instrument, which is called a catheter, through the hole into a blood vessel, and causing the catheter to reach the coronary artery of the heart where abnormality is identified.

In the coronary intervention, an irradiation position (an arm angle, SID (Source Image Distance), and FOV (Field Of View)), and the patient position (the position of a catheter table) are adjusted by an operator, such as a medical doctor or a technician. Consequently, the operator can proceed a maneuver, such as therapy or a test, while appropriately changing the irradiation position and the patient position.

For example, an X-ray diagnostic apparatus has been discussed that uses a catheter and that facilitates grasping a vascular structure around a target site, also facilitates the operation of the catheter, and reduces the test time and the therapeutic time.

In order to reduce exposure to the patient and operator during use of the X-ray diagnostic apparatus, it is desired that an X-ray diaphragm be set at an appropriate position to be irradiated with X-rays every time when the X-ray irradiation position is changed.

Unfortunately, manual setting of the irradiation position and the patient position during the test or therapy by the operator is a burden on the operator. Consequently, such setting is not performed in typical cases.

For example, a method, an apparatus and the like have been discussed that detect the distal end of a device, such as a catheter or a guidewire, and limit the irradiation region in the case where the patient is irradiated.

In the cases of the method and apparatus that limit the irradiation range, it is required to verify not only the distal end of the device to be operated but also the entire coronary artery, for example, whether the catheter provided at the entrance of the coronary artery is off or not, or whether the periphery of the coronary artery is blocked with a floating thrombus. Consequently, the currently discussed method and apparatus are applicable to a test or therapy for a patient only in restricted cases where there is no need to observe the entire coronary artery.

There is a technique referred to as spot fluoroscopy, which allows an operator to diagnose the patient more easily. Also in this case, the irradiation position at which the patient is irradiated with X-rays is required to be set, and it is assumed that not the entire coronary artery is viewable without movement of the X-ray diaphragm along with change in the imaging position.

To address this problem, in a test or therapy, an X-ray diagnostic apparatus is desired that irradiates an irradiation range to be automatically irradiated with X-rays, along with the change in information on the position of the system and the position of the patient during X-ray irradiation to the patient.

DETAILED DESCRIPTION

An X-ray diagnostic apparatus according to this embodiment includes: a memory circuitry configured to store a program; and a processing circuitry configured to read the program from the memory circuitry, and execute the program, wherein the processing circuitry is configured to identify a predetermined three-dimensional region of a patient at a predetermined position based on multiple X-ray images taken in at least two directions, and adjust an X-ray irradiation range based on the identified three-dimensional region and on system position information that includes irradiation position information where the patient is irradiated.

First Embodiment

An X-ray image diagnostic apparatus (X-ray diagnostic apparatus) according to a first embodiment is hereinafter described with reference to the accompanying drawings.

Figure 1:
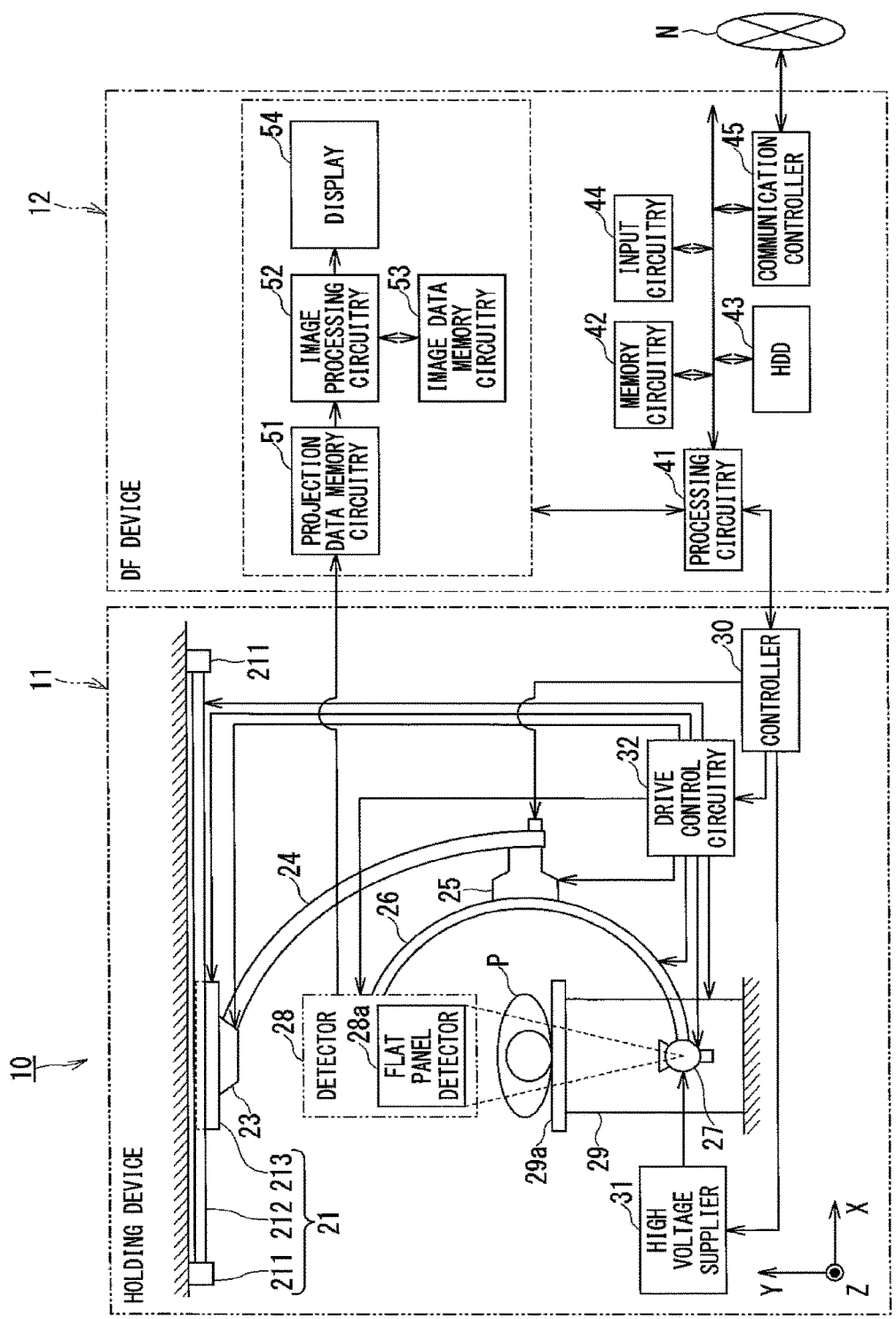
FIG. 1 is a schematic diagram showing a hardware configuration of an X-ray image diagnostic apparatus of a first embodiment.
Figure 2:
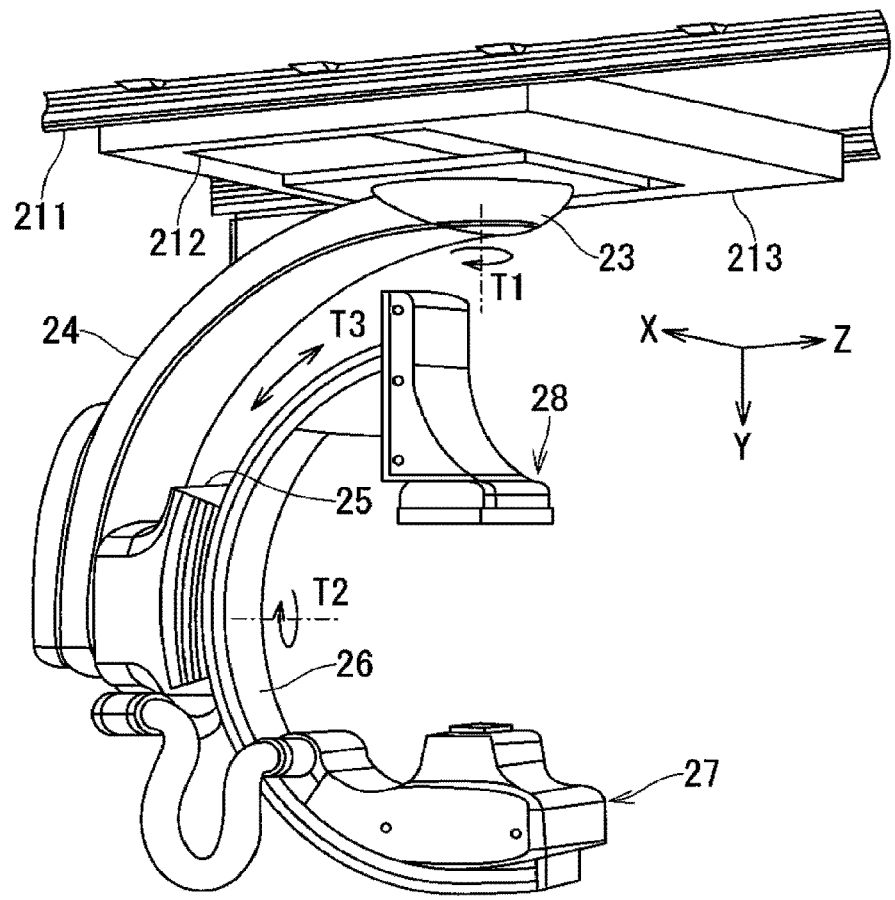
FIG. 2 is a perspective view showing an appearance configuration of a holding device in the X-ray image diagnostic apparatus of the first embodiment.

FIG. 1 is a schematic diagram showing a hardware configuration of the X-ray image diagnostic apparatus 10 according to the first embodiment. FIG. 2 is a perspective view showing an appearance configuration of a holding device 11 in the X-ray image diagnostic apparatus 10 of the first embodiment.

FIG. 1 shows the X-ray image diagnostic apparatus 10 that includes a ceiling-traveling C-arm of the first embodiment. The X-ray image diagnostic apparatus 10 roughly includes the holding device 11 and a digital fluorography (DF) device 12. In general, the holding device 11 and the DF device 12 are installed in a laboratory and a treatment room.

The X-ray image diagnostic apparatus 10 according to the first embodiment is not limited to the X-ray image diagnostic apparatus that includes the ceiling-traveling C-arm. This apparatus may be an X-ray image diagnostic apparatus that includes a floor-traveling C-arm, or an X-ray image diagnostic apparatus that includes a floor-standing C-arm. The description of the first embodiment is made using an exemplary X-ray image diagnostic apparatus that includes a C-arm. However, the apparatus is not limited to this example. For instance, an X-ray irradiator and an X-ray detector may be configured in a form held by respective arms independent of each other. Alternatively, the apparatus may be an X-ray image diagnostic apparatus that includes no C-arm.

The holding device 11 includes a sliding mechanism 21, a perpendicular axis turning mechanism 23, a suspension arm 24, a C-arm turning mechanism 25, a C-arm 26, an X-ray irradiator 27, a detector 28, a bed 29, a controller 30, a high voltage supplier 31, and a drive control circuitry 32.

The sliding mechanism 21 includes a Z-axis direction rail 211, an X-axis direction rail 212, and a vehicle 213. The sliding mechanism 21 is controlled by the controller 30 via the drive control circuitry 32 to slide the perpendicular axis turning mechanism 23, the suspension arm 24, the C-arm turning mechanism 25, the C-arm 26, the X-ray irradiator 27, and the detector 28 integrally in the horizontal direction.

The Z-axis direction rail 211 is arranged longitudinally in the Z-axis direction (the longitudinal axis direction of the top table 29a), and held on the ceiling.

The X-axis direction rail 212 is arranged in the X-axis direction (the short axis direction of the top table 29a), and held at rollers (not shown) at the opposite ends of this rail by the Z-axis direction rail 211. The X-axis direction rail 212 is controlled by the controller 30 via the drive control circuitry 32 to travel in the Z-axis direction on the Z-axis direction rail 211.

The vehicle 213 is held by the X-axis direction rail 212 via rollers (not shown). The vehicle 213 is controlled by the controller 30 via the drive control circuitry 32 to travel in the X-axis direction on the X-axis direction rail 212.

The X-axis direction rail 212 supporting the vehicle 213 is movable in the Z-axis direction on the Z-axis direction rail 211. The vehicle 213 is movable in the X-axis direction on the X-axis direction rail 212. Accordingly, the vehicle 213 is movable in the horizontal directions (X-axis and Z-axis directions) in the laboratory.

The perpendicular axis turning mechanism 23 is turnably supported by the vehicle 213. The perpendicular axis turning mechanism 23 is controlled by the controller 30 via the drive control circuitry 32 to turn the suspension arm 24, the C-arm turning mechanism 25, the C-arm 26, the X-ray irradiator 27 and the detector 28 integrally in a perpendicular axis turning direction T1 (shown in FIG. 2).

The suspension arm 24 is supported by the perpendicular axis turning mechanism 23.

The C-arm turning mechanism 25 is turnably supported by the suspension arm 24. The C-arm turning mechanism 25 is controlled by the controller 30 via the drive control circuitry 32 to turn the C-arm 26, the X-ray irradiator 27 and the detector 28 integrally in a turning direction T2 (show in FIG. 2) with respect to the suspension arm 24.

The C-arm 26 is supported by the C-arm turning mechanism 25, and allows the X-ray irradiator 27 and the detector 28 to be arranged opposite to each other centered on the test object P (patient P). The rear or a side surface of the C-arm 26 is provided with a rail (not shown). Through this rail sandwiched by the C-arm turning mechanism 25 and the C-arm 26, the C-arm 26 is controlled by the controller 30 via the drive control circuitry 32 to moves the X-ray irradiator 27 and the detector 28 integrally in an arc direction T3 (shown in FIG. 2) of the C-arm 26 along an arc locus.

The X-ray irradiator 27 is provided at one end of the C-arm 26. The X-ray irradiator 27 is arranged so as to be movable to and fro under control of the controller 30 via the drive control circuitry 32. The X-ray irradiator 27 includes an X-ray tube. This irradiator is supplied with high voltage power by the high voltage supplier 31 to irradiate a prescribed site of the test object P with X-rays according to the condition of the high voltage power. The X-ray irradiator 27 includes, on an X-ray emission side, an X-ray irradiation field stop diaphragm that includes multiple lead blades, and a compensation filter that is made up of silicone rubber for attenuating a predetermined amount of irradiation with X-rays so as to prevent halation.

The detector 28 is provided at the other end of the C-arm 26 on the emission side of the X-ray irradiator 27. The detector 28 is arranged so as to be movable to and fro under control of the controller 30 via the drive control circuitry 32. The detector 28 includes a flat panel detector (FPD) 28a, causes a two-dimensionally arranged detection element to detect X-rays, and thus converts the X-rays into a digital signal for each pixel.

The detector 28, which may be for example an I.I. (Image Intensifier)-TV system, may include an I.I., a TV camera, and an A/D (Analog to Digital) conversion circuit in this case. It is thus sufficient that the detector 28 can only detect the X-rays having passed through the test object P or directly entering X-rays.

The bed 29 is supported on the floor and, in turn, supports the top table (catheter table) 29a. The bed 29 is controlled by the controller 30 via the drive control circuitry 32 to move the top table 29a horizontally (in the X and Z-axes directions) and vertically (Y-axis direction) and rolls this table. The top table 29a allows the test object P to be mounted on this table, and is movable. The case of an under-tube type holding device 11 where the X-ray irradiator 27 is disposed below the top table 29a is described. Alternatively, this device may be an over-tube type holding device where the X-ray irradiator 27 is disposed above the top table 29a. Furthermore, a configuration may be adopted where an X-ray image diagnostic apparatus with no C-arm causes the bed 29 to drive the top table 29a.

The controller 30 includes a Central Processing Unit (CPU), not shown, and a memory. The controller 30 controls operations of the high voltage supplier 31, the drive control circuitry 32 and the like. The controller 30 controls the drive control circuitry 32, which drives the bed 29 and the top table 29a. This control can calculate bed 29 position information that represents the position of the bed 29, and top table 29a position information that indicates the position of the top table 29a.

The high voltage supplier 31 can supply the X-ray irradiator 27 with high voltage power according to control by the controller 30.

The drive control circuitry 32 can drive the sliding mechanism 21, the perpendicular axis turning mechanism 23, the C-arm turning mechanism 25, the C-arm 26, the X-ray irradiator 27, the detector 28, and the top table 29a of the bed 29, according to control by the controller 30.

The DF device 12 has a computer-based configuration, and can mutually communicate with a network N, such as a hospital backbone LAN (Local Area Network). The DF device 12 is made up of hardware that roughly includes a processing circuitry 41 as a processor, a memory circuitry 42, a HDD (Hard Disc Drive) 43, an input circuitry 44, a communication controller 45, a projection data memory circuitry 51, an image processing circuitry 52, an image data memory circuitry 53, and a display 54. The processing circuitry 41 is mutually connected to each of hardware configuration elements constituting the DF device 12, via a bus as a common signal transmission path. In some cases, the DF device 12 includes a drive (not shown) for a recording medium.

When an operator, such as a medical doctor or a medical technologist, operates the input circuitry 44 to input an instruction, the processing circuitry 41 executes a program stored in the memory circuitry 42. Alternatively, the processing circuitry 41 loads, on the memory circuitry 42, a program stored in a HDD 43, a program transferred from the network N, received by the communication controller 45 and installed in the HDD 43, or a program read from a recording medium inserted in a drive (not shown) for the recording medium and installed in the HDD 43, and then executes the program.

The memory circuitry 42 is a storing device having a configuration that includes configuration elements, which are both of ROM (Read Only Memory) and RAM (Random Access Memory). The memory circuitry 42 stores data that are IPL (Initial Program Loading) and BIOS (Basic Input/Output System), and is used as working memory of the processing circuitry 41 and for temporarily storing data.

The HDD 43 is a storing device having a configuration internally including a HD (Hard Disk) on which magnetic material is applied or vapor-deposited in an undetachable manner. The HDD 43 stores a program (including not only an application program but also an OS (Operating System)) installed in the DF device 12, and data. The OS may be configured to provide GUI (Graphical User Interface) that heavily uses graphics for displaying information for a test examiner and allows basic operations to be performed through the input circuitry 44.

The input circuitry 44 includes a keyboard, a mouse and the like that can be operated by an operator. Input signals according to operations are transmitted to the processing circuitry 41. The input circuitry 44 roughly includes a main console and a system console.

The term "processor" used in the above description means, for example, circuitry, such as a central processing unit (CPU), a graphics processing unit (GPU), an application specific integrated circuit (ASIC), a programmable logic device (e.g., simple programmable logic device (SPLD), complex programmable logic device (CPLD), a field programmable gate array (FPGA). FIG. 1 shows the case where one processing circuitry 41 as the processor is adopted. Alternatively, the number of processors may be two or more.

The processor achieves the functions by reading programs stored in the memory circuitry 42 or directly embedded in the circuitry of the processor and by executing the read programs. In the case where multiple processors are provided, the memory circuitry 42 for storing the programs may be provided separately for each processor. Alternatively, the memory circuitry 42 shown in FIG. 1 may be for storing programs corresponding to the functions of the respective processors.

The communication controller 45 performs communication control in conformity with specifications. The communication controller 45 has, for example, a function capable of connection with the network N via a telephone line, a dedicated line or the like. The DF device 12 can be connected to the network N via the communication controller 45.

The projection data memory circuitry 51 is controlled by the processing circuitry 41 to store projection data output from an A/D conversion circuit 28c of the holding device 11.

The image processing circuitry 52 is controlled by the processing circuitry 41 to generate data on a fluoroscopic image and a taken image (digital angiography (DA) image) from the projection data stored in the projection data memory circuitry 51. The image processing circuitry 52 applies image processing to the fluoroscopic image and the taken image stored in the image data memory circuitry 53. The image processing includes processes of enlarging, shading and spatially filtering data, processes of minimum-value-tracing and maximum-value-tracing data accumulated in time sequence, an adding process for removing noise, etc. Data after the image processing by the image processing circuitry 52 is output to the display 54 while being stored in a storing device, such as the image data memory circuitry 53.

The image data memory circuitry 53 is controlled by the processing circuitry 41 to store, as data, the fluoroscopic image and the taken image output from the image processing circuitry 52. The image data memory circuitry 53 stores the fluoroscopic image and the taken image before being subjected to image processing, which are referred to as original images and subjected to required image processing by the image processing circuitry 52 each time when an image is displayed on the display 54.

The display 54 is controlled by the processing circuitry 41 to superimpose test information (character information on parameters, a scale, etc.), such as a patient name, on the data of the fluoroscopic image and the taken image generated by the image processing circuitry 52, D/A-converts (digital-to-analog-converts) the combined signal, and subsequently displays the signal as a video signal. The display 54 may be a live monitor that displays live the fluoroscopic image and the taken image output from the image processing circuitry 52, a reference monitor that displays the taken image output from the image processing circuitry 52 as a still image or a moving reproduction image, and a system monitor that displays data for principally controlling the holding device 11, such as data for switching FOV (Field Of View).

Figure 3:
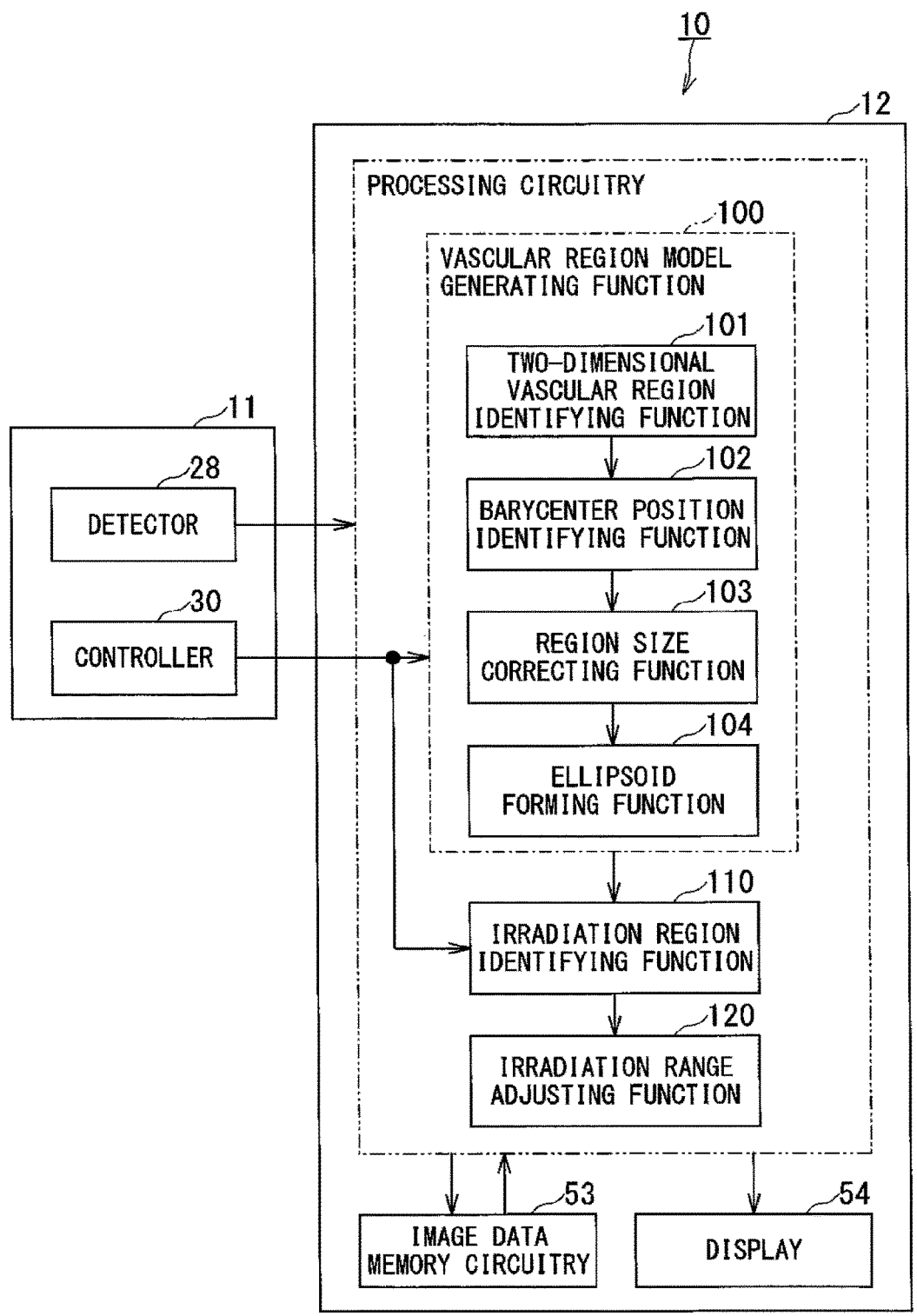
FIG. 3 is a block diagram showing functions of the X-ray image diagnostic apparatus of the first embodiment.

FIG. 3 is a block diagram showing the functions of the X-ray image diagnostic apparatus 10 of the first embodiment.

The processing circuitry 41 shown in FIG. 1 executes the programs, thereby allowing the DF device 12 to have a vascular (e.g., a blood vessel) region model generating function 100, an irradiation region identifying function 110, and an irradiation range adjusting function 120, as shown in FIG. 3.

That is, the processing circuitry 41 reads corresponding programs from the memory circuitry 42 or the HDD 43 and executes the programs, thereby allowing the vascular region model generating function 100, the irradiation region identifying function 110, and the irradiation range adjusting function 120 to be achieved.

The description is made assuming that the vascular region model generating function 100, the irradiation region identifying function 110 and the irradiation range adjusting function 120, the image data memory circuitry 53, and the display 54 are provided, as the functions of the X-ray image diagnostic apparatus 10, for the DF device 12. All or some of the vascular region model generating function 100, the irradiation region identifying function 110 and the irradiation range adjusting function 120, the image data memory circuitry 53, and the display 54 may be provided, as hardware, for the X-ray image diagnostic apparatus 10.

The vascular region model generating function 100 is a function that identifies a predetermined three-dimensional region of the patient P at a predetermined position on the basis of multiple X-ray images taken in at least two directions. For example, the vascular region model generating function 100 identifies the vascular region of the patient P at a spatial position on the top table 29a. The vascular region model generating function 100 then generates a virtual three-dimensional model that represents the identified vascular region. In this case, the vascular region model generating function 100 includes a two-dimensional vascular region identifying function 101, a barycenter position identifying function 102, a region size correcting function 103, and an ellipsoid forming function 104.

Here, the predetermined position is, for example, a position of spatial coordinates assigned onto the top table 29a, and is the position of the vascular region of the patient P. The spatial coordinates can be used as an example. However, this embodiment is not limited to the case of the spatial coordinates. Thus, this embodiment encompasses the case of identifying the position of the vascular region of the patient P as the spatial position. The vascular region of the patient P at the spatial position may also be identified as a spatial position in a system (e.g., the X-ray image diagnostic apparatus 10) according to the relative positional relationship of the system.

The spatial position is shown as a position on the top table 29a as an example. However, the position is not limited thereto. For example, in the case of imaging the patient P at the standing position, the vascular region of the patient P at the spatial position may be identified on the basis of the distance from the floor with reference to the floor.

The description is made using a vascular region at the periphery of the heart including the coronary artery as an example. However, this embodiment is not limited to the case of the vascular region at the periphery of the heart including the coronary artery. The vascular region that can be a target is any site having a certain region in a human body.

The two-dimensional vascular region identifying function 101 is a function that identifies the two-dimensional vascular region from multiple X-ray images of the patient P, on the basis of multiple X-ray images, which have been taken in at least two directions. For example, the two-dimensional vascular region identifying function 101 identifies the two-dimensional vascular region using the contrast images taken in the multiple directions. The contrast image is a vascular contrast image taken by contrast imaging.

The barycenter position identifying function 102 is a function of identifying the barycenter position of the two-dimensional vascular region.

The region size correcting function 103 is a function of correcting the sizes of the two-dimensional vascular regions.

The ellipsoid forming function 104 is a function that arranges the barycenter positions of the identified two-dimensional vascular regions at the center position of the imaging target of the patient P, and determines a virtual three-dimensional model. For example, the ellipsoid forming function 104 generates the virtual three-dimensional model from the arranged two-dimensional vascular regions. Thus, the ellipsoid forming function 104 can identify the three-dimensional vascular region of the patient P on the basis of the virtual ellipsoid at the spatial position on the top table 29a, using the generated virtual three-dimensional model.

During identifying the virtual three-dimensional model, the vascular region model generating function 100 may identify the virtual three-dimensional model of patient P on the top table 29a, on the basis of patient characteristic information that represents the characteristics of the patient P, and of patient position information that represents the position of the patient P. Use of such information can identify more highly accurate three-dimensional model, and more correctly identify the irradiation region where the patient P is irradiated.

The patient characteristic information represents, for example, information on the height from the top table 29a to the center of the heart, including the thickness of a mat laid on the top table 29a. The information on the height can be calculated, for example, from the body thickness or set on the basis of previously obtained CT or MRI scanning information.

Next, the irradiation region identifying function 110 is a function of identifying the irradiation region where the patient P is irradiated, through a pseudo irradiation region of the three-dimensional model, on the basis of the virtual three-dimensional model generated by the vascular region model generating function 100, and of system position information that includes information on the irradiation position where the patient P is irradiated. For example, the irradiation region identifying function 110 changes the pseudo irradiation region of the three-dimensional model along with change in information pertaining to the system position information, and identifies the irradiation region where the patient P is irradiated according to the change.

Here, the system position information is position information on the system when the X-ray image diagnostic apparatus 10 irradiates the patient P with X-rays. The system position information may include, for example, the irradiation position information and the patient position information. The irradiation position information includes information, such as on the arm angle representing the angle of the C-arm 26, the source image distance (SID), and FOV. The patient position information includes information on the top table 29a (information pertaining to the height and thickness of the catheter table etc.) and on information pertaining to the inclination of the top table 29a (e.g., what is called a longitudinal tilt and a lateral tilt).

Next, the irradiation range adjusting function 120 is a function of adjusting the X-ray irradiation range so as to allow the identified irradiation region to be irradiated with X-rays. For example, the irradiation range adjusting function 120 controls the X-ray diaphragm included in the X-ray irradiator 27 through the controller 30 to adjust the X-ray irradiation range so as to allow the identified irradiation region to be irradiated with X-rays. The irradiation range adjusting function 120 may attenuate X-rays using a compensation filter included in the X-ray irradiator 27, through the controller 30.

The description has been made on this embodiment such that the irradiation region identifying function 110 and the irradiation range adjusting function 120 should be achieved to have the respective functions. However, this embodiment is not limited thereto. For example, the irradiation region identifying function 110 may be included in the irradiation range adjusting function 120. Alternatively, the irradiation range adjusting function 120 may be included in the irradiation region identifying function 110. In this case, this embodiment may be achieved by a single configuration element that includes the irradiation region identifying function 110 and the irradiation range adjusting function 120.

Irradiation Range Automatic Control Process

Figure 4:
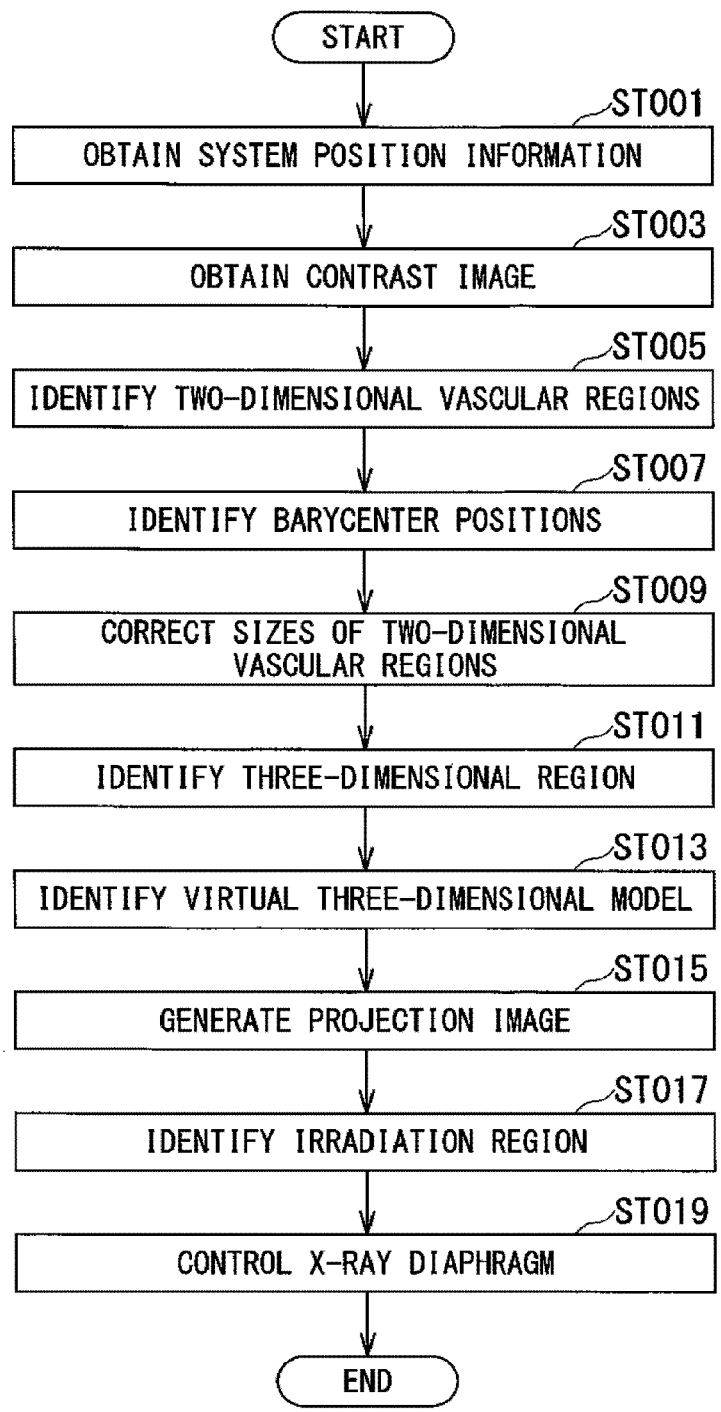
FIG. 4 is a flowchart showing an irradiation range automatic control process during the X-ray image diagnostic apparatus according to the first embodiment irradiating a vascular region of a patient with X-rays.

Next, an irradiation range automatic control process of the X-ray image diagnostic apparatus 10 according to the first embodiment is described using a flowchart shown in FIG. 4 with reference to FIGS. 1 to 3.

FIG. 4 is the flowchart showing the irradiation range automatic control process during the X-ray image diagnostic apparatus 10 according to the first embodiment irradiating a vascular region of the patient P with X-rays.

First, the DF device 12 of the X-ray image diagnostic apparatus 10 obtains the system position information pertaining to the X-ray image diagnostic apparatus 10 through the controller 30 of the holding device 11 (step STOOL). In this embodiment, the system position information includes the information on the irradiation position where the patient P is irradiated. The irradiation position information in the system position information includes information, such as on the angel of the C-arm 26, SID, and FOV. The system position information may further include the patient position information that represents the position of the patient P.

The DF device 12 of the X-ray image diagnostic apparatus 10 stores the contrast image and the taken image in the image data memory circuitry 53. The processing circuitry 41 then causes the vascular region model generating function 100 to obtain the contrast image from the image data memory circuitry 53, for example (step ST003).

The X-ray image diagnostic apparatus 10 necessarily performs follow-up imaging and X-ray imaging in multiple directions at an initial stage of the maneuver. Consequently, in this embodiment, additional contrast imaging is unnecessary. That is, normal follow-up imaging can obtain the contrast images taken in at least two directions. Thus, the contrast images taken in multiple directions are available. Consequently, in this embodiment, the multiple contrast images are preliminarily stored in the image data memory circuitry 53, the processing circuitry 41 causes the vascular region model generating function 100 to obtain the multiple contrast images stored in the image data memory circuitry 53.

The follow-up imaging is a process of taking images before and after injection of a contrast medium, and verifying the vascular region into which the contrast medium has been injected. The contrast image may be a fluoroscopic image in which the vascular region of the patient P is being projected while the contrast medium is being injected. Provided that one vascular region is taken as one cut, at least two cuts in different imaging directions are taken. The more the number of imaged cuts, the more highly the virtual three-dimensional model is generated.

In some cases, the angle and order of taking images are preliminarily defined for each hospital. This is applicable to this embodiment in the case where the images are taken in multiple directions and contain a vascular region of the patient P to be taken or a vascular region having a certain size. Hereinafter, a vascular region at the periphery of the heart including the coronary artery is described.

Next, the DF device 12 of the X-ray image diagnostic apparatus 10 identifies the two-dimensional vascular regions of the patient P (step ST005). For example, the processing circuitry 41 causes the two-dimensional vascular region identifying function 101 to identify the two-dimensional vascular regions from the respective contrast images of the patient P taken in the multiple directions.

Figure 5:
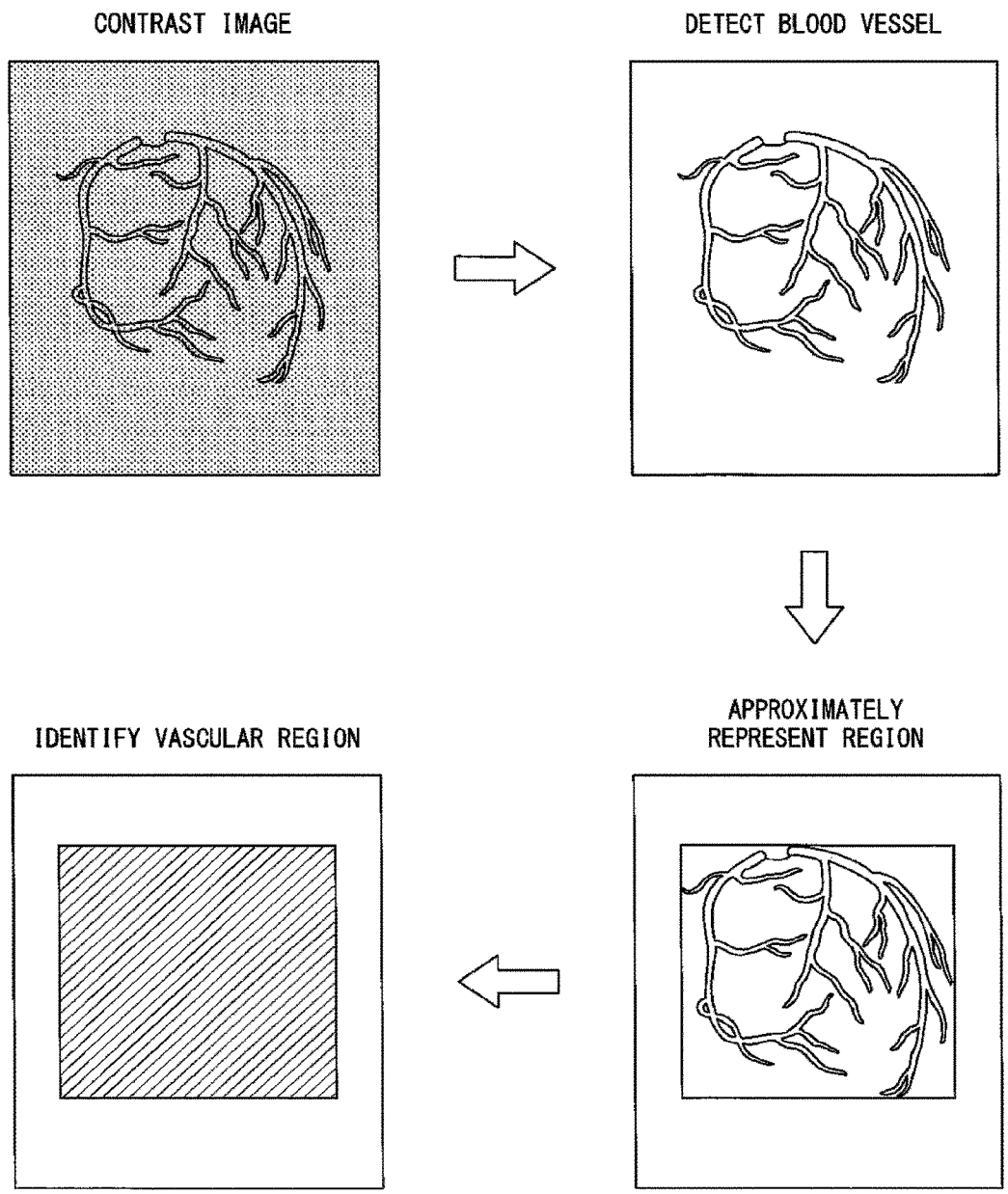
FIG. 5 is a diagram illustrating a process of causing a two-dimensional vascular region identifying function of the X-ray image diagnostic apparatus according to the first embodiment to identify a two-dimensional vascular region of the patient from one contrast image.

FIG. 5 is a diagram illustrating a process of causing the two-dimensional vascular region identifying function 101 of the X-ray image diagnostic apparatus 10 according to this embodiment to identify a two-dimensional vascular region of the patient P from one contrast image.

As shown in FIG. 5, the processing circuitry 41 causes the two-dimensional vascular region identifying function 101 to detect a blood vessel constituting the coronary artery from one contrast image, and approximately represent the region including the blood vessel as, for example, a rectangle. The region approximately represented as the rectangle by the two-dimensional vascular region identifying function 101 is identified as a vascular region in two-dimensional representation, which is called a two-dimensional vascular region.

The two-dimensional vascular region identifying function 101 approximately represents the two-dimensional vascular regions from the respective contrast images, and identifies the vascular regions as the two-dimensional vascular regions. The approximately represented shape is not limited to the rectangle. For example, in the case where the aperture blades of the X-ray diaphragm move vertically and horizontally but do not turn, approximate representation of the region as the rectangle is sufficiently applicable. On the contrary, in the case where the aperture blades of the X-ray diaphragm are turnable, approximate representation of the region as a substantially circular shape is applicable. The shape in this case is a shape for blocking a region without need of irradiation. The shape is not limited to the rectangle and the substantially circular shape.

As described above, the processing circuitry 41 can cause the two-dimensional vascular region identifying function 101 to identify the two-dimensional vascular regions of the patient P from the respective contrast images taken in the multiple directions.

Figure 6:
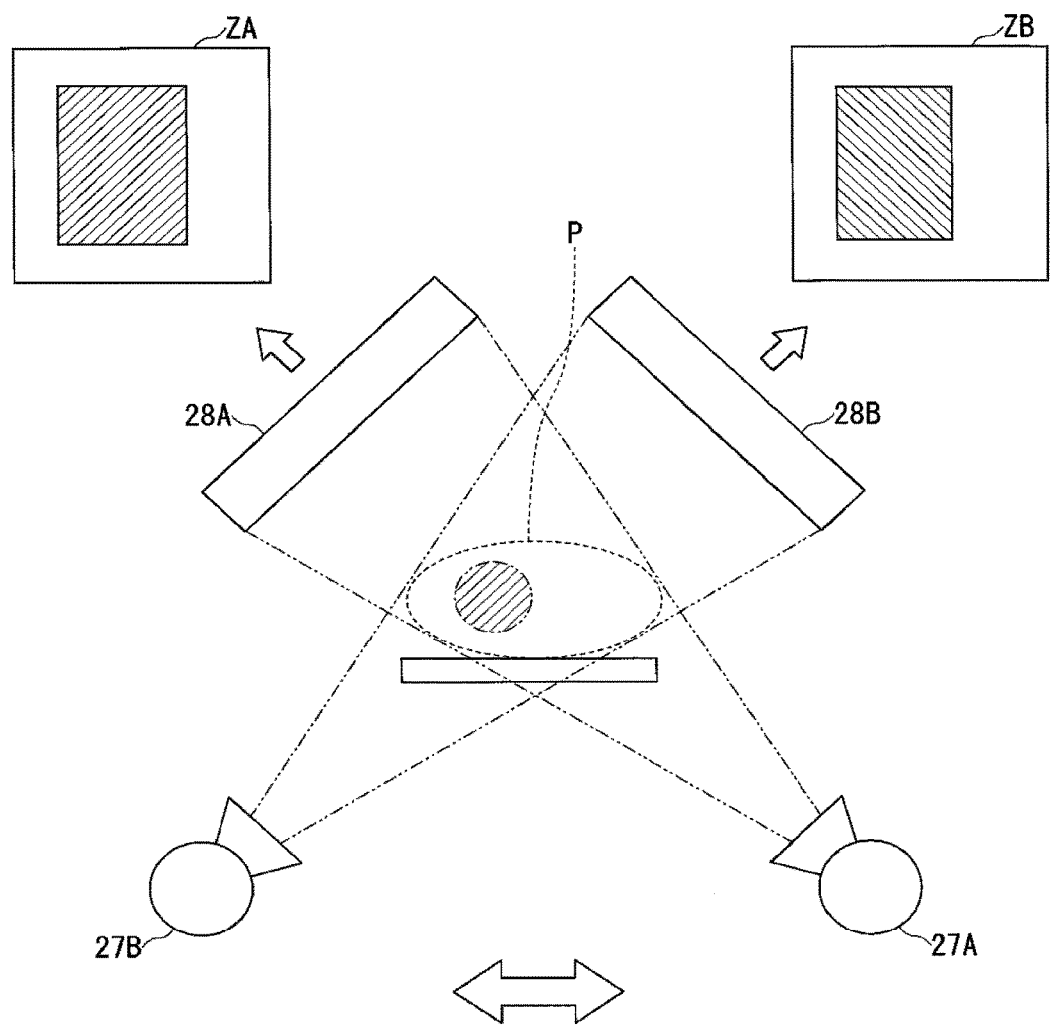
FIG. 6 is a diagram illustrating identification of the two-dimensional vascular region from contrast images taken by irradiating the patient with X-rays in two directions in the X-ray image diagnostic apparatus according to the first embodiment.

FIG. 6 is a diagram illustrating identification of the two-dimensional vascular region from contrast images taken by irradiating the patient P with X-rays in two directions in the X-ray image diagnostic apparatus 10 according to the first embodiment.

As shown in FIG. 6, when the X-ray irradiator 27 is at the position of the X-ray irradiator 27A and the detector 28 is at the position of the detector 28A and the patient P is irradiated with X-rays, the two-dimensional vascular region of the patient P is identified in a contrast image ZA. When the X-ray irradiator 27 is at the position of the X-ray irradiator 27B and the detector 28 is at the position of the detector 28B and the patient P is irradiated with X-rays, the two-dimensional vascular region of the patient P is identified in a contrast image ZB.

Thus, the processing circuitry 41 causes the two-dimensional vascular region identifying function 101 to identify the two-dimensional vascular regions in the respective irradiation directions from the obtained contrast images.

Next, the DF device 12 of the X-ray image diagnostic apparatus 10 identifies the barycenter positions of the two-dimensional vascular regions (step ST007). For example, the processing circuitry 41 causes the barycenter position identifying function 102 to identify the barycenter positions of the respective two-dimensional vascular regions identified by the two-dimensional vascular region identifying function 101.

The DF device 12 of the X-ray image diagnostic apparatus 10 corrects each of the sizes of the two-dimensional vascular regions (step ST009). For example, the processing circuitry 41 causes the region size correcting function 103 to correct the two-dimensional vascular regions on the contrast images to have the respective sizes at spatial positions on the top table 29a.

Referring to FIG. 6, for example, in comparison between the contrast images ZA and ZB, the two-dimensional vascular region in the contrast image ZA and the two-dimensional vascular region in the contrast image ZB have different sizes. This is because the scale of enlargement of images is different according to the SID, FOV, patient position information and the like.

The region size correcting function 103 corrects the two-dimensional vascular region of the contrast image ZA to have the size at the spatial position on the top table 29a, while correcting the two-dimensional vascular region of the contrast image ZB to have the size at the spatial position on the top table 29a. Consequently, the size of the two-dimensional vascular region in the corrected contrast image ZA and the size of the two-dimensional vascular region in the corrected contrast image ZB become the corresponding size of the three-dimensional model with respect to the spatial position on the top table 29a.

Next, the DF device 12 of the X-ray image diagnostic apparatus 10 aligns the barycenter positions of the respective two-dimensional vascular regions, and identifies the region that represents the virtual vascular region of the patient P (three-dimensional region) (step ST011). For example, the processing circuitry 41 causes the vascular region model generating function 100 to align the barycenter position of the two-dimensional vascular region in the contrast image ZA and the two-dimensional vascular region in the contrast image ZB, and identify the virtual three-dimensional vascular region corresponding to the three-dimensional vascular region of the patient P on at the spatial position on the top table 29a.

The DF device 12 of the X-ray image diagnostic apparatus 10 identifies the three-dimensional vascular region (three-dimensional region) of the patient P at the spatial position on the top table 29a using the virtual three-dimensional model (step ST013). For example, the processing circuitry 41 causes the ellipsoid forming function 104 to identify the virtual three-dimensional vascular region of the patient P at the spatial position on the top table 29a using the virtual ellipsoid.

In this case, the processing circuitry 41 causes the ellipsoid forming function 104 to identify the three-dimensional vascular region of the patient P at the spatial position on the top table 29a using the virtual ellipsoid on the basis of the three-dimensional region indicated by the sizes of the two-dimensional vascular regions in the corrected contrast images ZA and ZB.

In other words, the ellipsoid forming function 104 estimates an ellipsoid circumscribed to the three-dimensional region identified at the spatial position on the top table 29a, and identifies the virtual three-dimensional vascular region of the patient P using the virtual ellipsoid.

Figure 7:
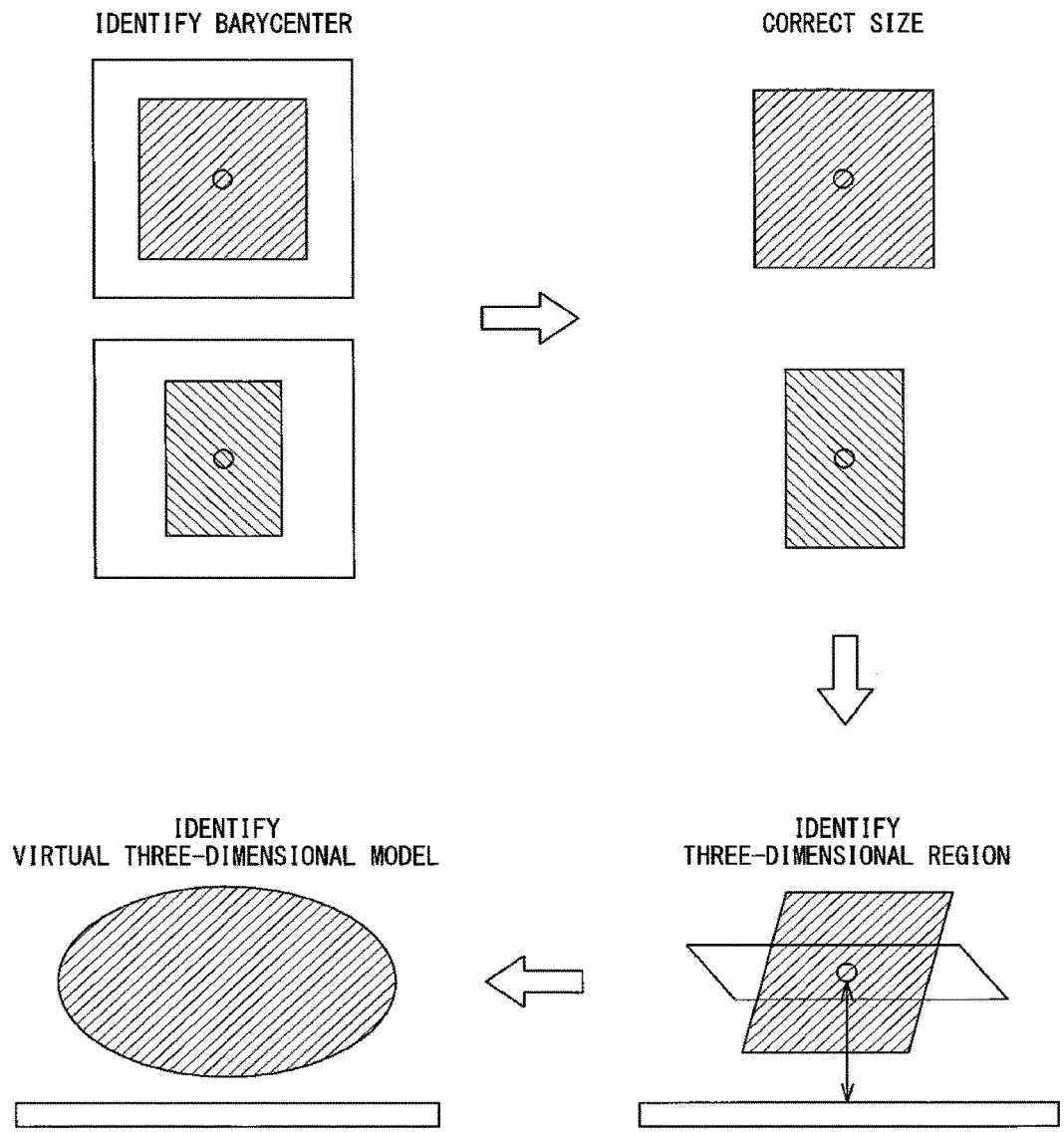
FIG. 7 is a diagram schematically illustrating the details of processes executed from step ST007 to step ST013 by a DF device of the X-ray image diagnostic apparatus according to the first embodiment.

FIG. 7 is a diagram schematically illustrating the details of processes executed from step ST007 to step ST013 by the DF device 12 of the X-ray image diagnostic apparatus 10 according to the first embodiment.

As shown in FIG. 7, the DF device 12 of the X-ray image diagnostic apparatus 10 according to the first embodiment causes the vascular region model generating function 100 to identify the two-dimensional vascular regions from the contrast images, and identify the barycenter positions of the two-dimensional vascular regions. Next, the vascular region model generating function 100 corrects the sizes of the two-dimensional vascular regions, and identifies each three-dimensional region at the spatial position on the top table 29a, thereby identifying the virtual three-dimensional vascular region of the patient P using the ellipsoid, which is a three-dimensional model.

The processing circuitry 41 thus causes the ellipsoid forming function 104 to identify the three-dimensional vascular region of the patient P by means of the virtual ellipsoid. However, this embodiment is not limited to the ellipsoid. For example, a substantially ellipsoidal shape may be identified from the shape in the two-dimensional vascular region. Alternatively, the three-dimensional vascular region may be identified using a substantially cubic shape or a substantially rectangular parallelepiped shape that is made up of a three-dimensional shape similar to the shape of the vascular region.

Next, the DF device 12 of the X-ray image diagnostic apparatus 10 generates a projection image of the vascular region of the patient P (step ST015). For example, the processing circuitry 41 causes the irradiation region identifying function 110 generates the projection image where an elliptical three-dimensional model is irradiated on the basis of the three-dimensional model identified in step ST013 and of the system position information including the information on the irradiation position where the patient P is irradiated.

Here, the projection image is a three-dimensional image (rendering image) displayed as a two-dimensional image in a three-dimensional manner. In an example, the projection image is displayed as a three-dimensional image. This embodiment is not limited to the three-dimensional image, which may be a two-dimensional image instead. That is, in this embodiment, a three-dimensional model or a two-dimensional model of the vascular region of the patient P at the spatial position on the top table 29a is applicable as the projection image by means of the image projected on the information on the two-dimensional plane.

The DF device 12 of the X-ray image diagnostic apparatus 10 uses the irradiation position information to generate the projection image in real time along with change in the arm angle of the C-arm 26 that irradiates the patient P with X-rays, SID and FOV. The DF device 12 generates the projection image in real time every time when the information pertaining to the top table 29a and the information pertaining to the inclination of the top table 29a in the patient position information are changed. The information pertaining to the top table 29a is, for example, information pertaining to the height and thickness of the catheter table and the like. The inclination of the top table 29a is, for example, what is called a longitudinal tilt or lateral tilt.

The DF device 12 of the X-ray image diagnostic apparatus 10 identifies the irradiation region in the generated projection image (step ST017). For example, the processing circuitry 41 causes the irradiation region identifying function 110 to identify an outer frame of the vascular region of the projection image as the irradiation region of the patient P. The irradiation region identifying function 110 can generate the projection image of the identified three-dimensional model on the basis of the changeable system position information. Consequently, the outer frame of the vascular region of the projection image is used to identify the irradiation region of the patient P.

The projection image is not necessarily displayed on the display 54. However, as the projection image is generated from the three-dimensional model along with change in system position information, a real-time display function may be provided to allow the generated projection image to be displayed together with the contrast image of the patient P. In this case, the generated projection image can be displayed as a virtual collimator.

Next, the DF device 12 of the X-ray image diagnostic apparatus 10 controls the X-ray diaphragm to adjust the X-ray irradiation range, and causes the X-ray irradiator 27 to irradiate the patient P (step ST019). For example, the processing circuitry 41 causes the irradiation range adjusting function 120 to control the X-ray diaphragm included in the X-ray irradiator 27 through the controller 30 to thereby adjust the X-ray irradiation range so as to allow the identified irradiation region to be irradiated with X-rays. In this case, X-rays can be blocked from regions other than the irradiation region identified in step ST017.

The irradiation range adjusting function 120 of the DF device 12 may use a compensation filter included in the X-ray irradiator 27, through the controller 30. In this case, the irradiation range adjusting function 120 can limit the irradiation so as to prevent the regions other than the identified irradiation region from being irradiated while attenuating the X-ray in conformity with the shape of the vascular region of the projection image.

Figure 8A:
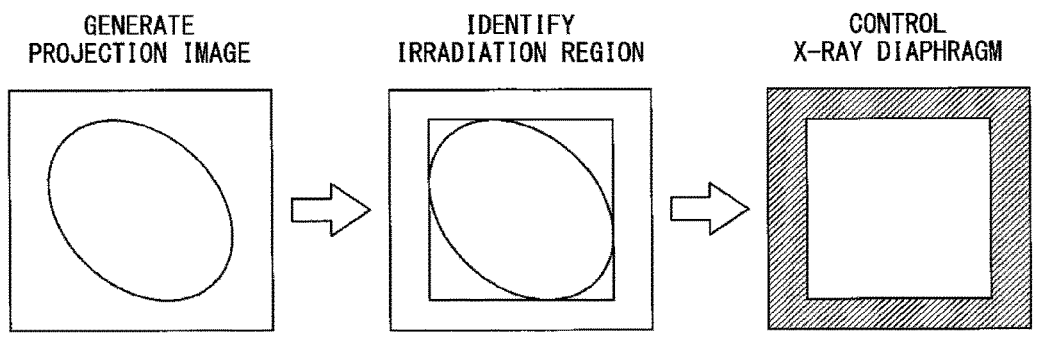
FIGS. 8A, 8B and 8C are diagrams schematically illustrating the details of processes executed from step ST015 to step ST019 by the DF device of the X-ray image diagnostic apparatus according to the first embodiment.
Figure 8B:
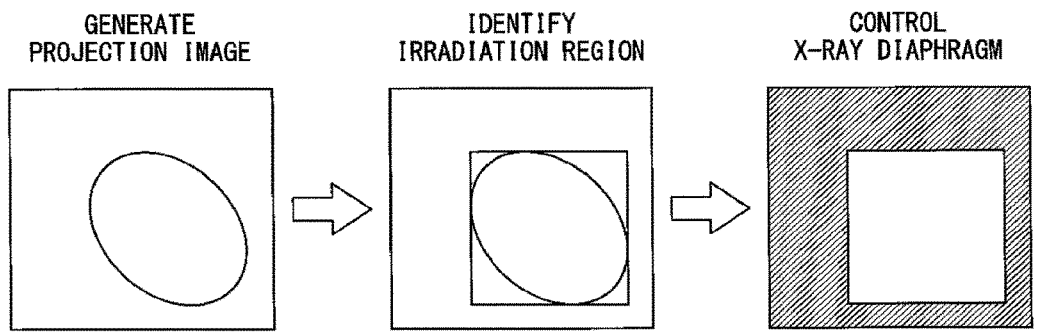
Figure 8C:
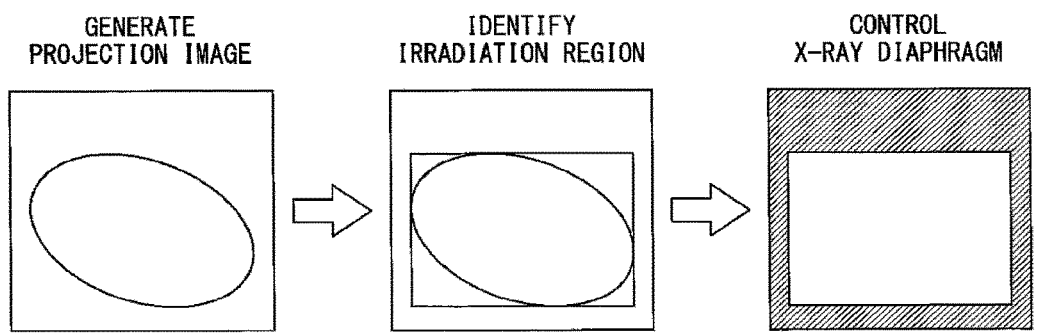

FIGS. 8A, 8B and 8C are diagrams schematically illustrating the details of processes executed from step ST015 to step ST019 by the DF device 12 of the X-ray image diagnostic apparatus 10 according to the first embodiment.

FIGS. 8A, 8B and 8C shows that the DF device 12 of the X-ray image diagnostic apparatus 10 according to the first embodiment generates the projection image on the basis of the three-dimensional model of the ellipsoid identified in step ST013, and identifies, as the irradiation region, the rectangular region circumscribed to the vascular region of the projection image. The irradiation range adjusting function 120 of the DF device 12 controls the X-ray diaphragm in conformity with the rectangular region circumscribed to the vascular region of the projection image, thereby allowing the X-rays to be blocked from leaving the identified irradiation region.

Consequently, in this embodiment, the exposure dose of irradiation to the patient P can be attenuated. The process of irradiating the patient P with X-rays is applicable to fluoroscopy with low exposure dose and also to imaging with high exposure dose in the same manner.

FIGS. 8A, 8B and 8C show that every time when the irradiation position information or the system position information is changed, the projection image is generated. For example, when the patient position information is changed, the system position information is simultaneously changed. Consequently, upon each change, the DF device 12 of the X-ray image diagnostic apparatus 10 automatically generates the projection image of the three-dimensional model in a manner from FIG. 8A to FIG. 8B or from FIG. 8B to FIG. 8C, and automatically controls the X-ray diaphragm of the irradiation region.

Once the virtual three-dimensional model is generated, this virtual three-dimensional model can still be used to generate the projection image without regenerate or change this virtual three-dimensional model.

The X-ray image diagnostic apparatus 10 according to this embodiment continuously executes the irradiation range automatic control process during X-ray irradiation, and finishes the irradiation range automatic control process after the maneuver is finished.

As described above, the X-ray image diagnostic apparatus 10 according to the first embodiment causes the vascular region model generating function 100 to identify the vascular region of the patient P at the spatial position on the top table 29a, and generates the virtual three-dimensional model representing the identified vascular region. The X-ray image diagnostic apparatus 10 causes the irradiation region identifying function 110 to adjust the X-ray irradiation range along with change in information pertaining to the system position information, on the basis of the generated virtual three-dimensional model and of the system position information including the information on the irradiation position where the patient P is irradiated.

The X-ray image diagnostic apparatus 10 according to the first embodiment causes the irradiation range adjusting function 120 to adjust the X-ray irradiation range so as to irradiate the irradiation region identified by the three-dimensional model with X-rays. Consequently, in a test or therapy, the apparatus can identify the irradiation region to be automatically irradiated, along with the change in information on the position of the system and the position of the patient during X-ray irradiation to the patient P, and irradiate the irradiation region with X-rays.

Therefore, the X-ray image diagnostic apparatus 10 according to the first embodiment can avoid unnecessary X-ray irradiation, which can reduce the exposure of the patient P. When the operator performs X-ray irradiation, the operator is not required to manually set the irradiation position and the patient position. Consequently, the load due to reduction in exposure of the patient P can be reduced.

Furthermore, the X-ray image diagnostic apparatus 10 according to the first embodiment thus causes the two-dimensional vascular region identifying function 101 to identify the two-dimensional vascular regions from the respective contrast images of the patient P taken in the multiple directions. However, the first embodiment is not limited thereto. The fluoroscopic image and the taken image obtained on the basis of X-ray irradiation to the patient P may be applied as the contrast image in step ST003.

For example, the X-ray image diagnostic apparatus 10 according to the first embodiment can obtain the fluoroscopic image or the taken image by performing fluoroscopy or imaging of the patient P in step ST019. The DF device 12 of the X-ray image diagnostic apparatus 10 can update and correct the shape of the ellipsoid that forms the vascular region, by adopting the obtained fluoroscopic image or taken image as the contrast image in step ST003.

In the first embodiment, when the vascular region is determined, the ellipsoid is identified using the contrast image of follow-up imaging. Here, the vascular region can be identified more accurately by causing identification of the ellipsoid to reflect the fluoroscopic image or the taken image.

In step ST017, the X-ray image diagnostic apparatus 10 according to the first embodiment causes the irradiation region identifying function 110 to identify the irradiation region of the generated projection image. However, this embodiment is not limited thereto. For example, the irradiation region identifying function 110 may three-dimensionally set a region of interest (ROI) in the projection image. In this case, the irradiation region identifying function 110 may have a configuration of irradiating the set ROI with X-rays.

Furthermore, for example, the X-ray image diagnostic apparatus 10 according to the first embodiment may store the identified three-dimensional model, thereby allowing this virtual three-dimensional model to be used for imaging of the patient P at the second time and thereafter. Moreover, the X-ray image diagnostic apparatus 10 may apply a three-dimensional model identified by what is other than the X-ray image diagnostic apparatus 10 to a test by the X-ray image diagnostic apparatus 10.

For example, in the case of using the virtual three-dimensional model identified in step ST013 at the second time and thereafter, the virtual three-dimensional model is aligned with the patient on the basis of the image obtained by taking an image of the patient P at least one time, thereby allowing the X-ray image diagnostic apparatus 10 to automatically adjust the X-ray irradiation range where the patient P is irradiated. Any of images of follow-up imaging and contrast imaging may be applied to alignment of the three-dimensional model, which is not specifically limited.

As described above, the X-ray image diagnostic apparatus 10 can omit the processes of identifying the three-dimensional model in steps ST003 to ST013. The apparatus can adjust the X-ray irradiation range where the patient P is irradiated, by aligning the stored three-dimensional model with the patient P. Likewise, even in the case of the three-dimensional model identified by what is other than the X-ray image diagnostic apparatus 10, the X-ray irradiation range where the patient P is irradiated can be adjusted by aligning the identified three-dimensional model with the patient P.

Second Embodiment

In a second embodiment, the X-ray image diagnostic apparatus 10, basically having been described in the first embodiment, causes the vascular region model generating function 100 to identify the two-dimensional vascular regions from the contrast images varying with heartbeat, and identify the three-dimensional vascular region from each of the two-dimensional vascular regions.

Here, the coronary artery of patient P varies with heartbeat. Furthermore, the artery varies also with respiration. In contrast images, the vascular regions thus vary with heartbeat and the phase of respiration. Consequently, a two-dimensional vascular region in consideration with a margin can be identified on the basis of the heart beat and respiration.

For example, contrast images with expiration in the diastolic phase of heartbeat and inspiration in the diastolic phase of heartbeat are used to identify a two-dimensional vascular region so as to include the vascular regions in every case. Thus, the two-dimensional vascular region in consideration with the margin based on heartbeat and respiration can be identified.

Furthermore, one cut of a contrast image may be subjected to a bottom trace process to identify the two-dimensional vascular region. For example, the X-ray image diagnostic apparatus 10 obtains multiple contrast images in time sequence while injecting the contrast medium into the patient P. The vascular region model generating function 100 may execute the process (bottom trace process) of tracing the obtained multiple contrast images in the temporal direction, and identify the two-dimensional vascular region.

Third Embodiment

A third embodiment is an apparatus according to the X-ray image diagnostic apparatus 10 according to the first embodiment, and causes the vascular region model generating function 100 to detect the distal end of a vascular insertion device in a vascular region, and causes the irradiation region identifying function 110 to detect the distal end of the vascular insertion device in the irradiation region, and project the distal end position of the vascular insertion device onto the projection image.

Thus, according to the third embodiment, the processing circuitry 41 allows the irradiation region identifying function 110 to project the distal end position of the vascular insertion device onto the projection image. Consequently, the vascular insertion device in the projection image and the vascular insertion device in a live image during X-ray irradiation can be compared with each other in real time. In this case, when the vascular insertion device in the projection image and the vascular insertion device in the live image during X-ray irradiation deviate from each other, it is determined that the patient P has moved on the top table 29a, and the deviation can be automatically corrected.

For example, when the X-ray image diagnostic apparatus 10 according to third embodiment detects the deviation, the processing circuitry 41 causes the irradiation region identifying function 110 to correct the position of the virtual three-dimensional model on the top table 29a. The irradiation range adjusting function 120 adjusts the X-ray irradiation range where the patient P is irradiated in a state where the vascular insertion device in the live image during X-ray irradiation and the vascular insertion device in the projection image coincide with each other.

Thus, even when the patient P moves on the top table 29a, the X-ray image diagnostic apparatus 10 according to the third embodiment can automatically correct the X-ray irradiation region to adjust this X-ray irradiation range. Consequently, the exposure to the patient P due to X-ray irradiation range can be attenuated without requirement of any operational burden on the operator.

The vascular insertion device may be any of a catheter, a guidewire, a stent, and a balloon. The vascular insertion device may be any device to be inserted into the body of the patient P. However, the device is not limited thereto.

Although some embodiments of the present invention have been described, these embodiments have been presented only as examples, which are not intended to limit the scope of the invention. These embodiments can be achieved in various other forms. Omission, replacement, and change in various forms can be achieved in a range without deviating from the gist of the invention. These embodiments and variations are included in the scope and gist of the invention, and also in the invention described in the claims and their equivalent ranges in a similar manner.

What is claimed is:

1. An X-ray diagnostic apparatus, comprising:
a memory to store a program; and
processing circuitry configured to read the program from the memory, and execute the program,
wherein, by executing the program, the processing circuitry is configured to
identify two-dimensional vascular regions in corresponding X-ray images taken in at least two directions,
correct a size of each of the vascular regions on corresponding each of the X-ray images so as to have a corresponding size at a spatial position on a top table on which a patient is mounted,
identify a three-dimensional region of the patient at the spatial position on the top table based on the corrected vascular regions, and adjust an X-ray irradiation range by controlling an X-ray diaphragm, or attenuate X-ray irradiation to a region other than the identified three-dimensional region by controlling a filter, based on the identified three-dimensional region and based on system position information that includes irradiation position information indicating where the patient is irradiated.

2. The X-ray diagnostic apparatus according to claim 1, wherein the processing circuitry is further configured to adjust the X-ray irradiation range along with a change in information pertaining to the system position information.

3. The X-ray diagnostic apparatus according to claim 1, wherein the X-ray images are vascular contrast images.

4. The X-ray diagnostic apparatus according to claim 3, wherein the processing circuitry is further configured to
identify a vascular region of the patient in each of the vascular contrast images based on the vascular contrast images,
correct a size of each of the vascular regions on the corresponding each of the vascular contrast images so as to have a corresponding size at the spatial position on the top table on which a patient is mounted,
identify the three-dimensional region of the patient at the spatial position on the top table based on the corrected vascular regions,
generate a three-dimensional model that includes the identified three-dimensional region, and
identify an irradiation range where the patient is irradiated, along with a change in the system position information, based on the generated three-dimensional model and the system position information, and adjust the X-ray irradiation range.

5. The X-ray diagnostic apparatus according to claim 4, wherein the processing circuitry is further configured to identify barycenter positions of the corrected vascular regions, arrange the barycenter positions of the corrected vascular regions at a center position of an imaging target of the patient, and generate the three-dimensional model.

6. The X-ray diagnostic apparatus according to claim 4, wherein the processing circuitry is further configured to identify the three-dimensional region by an ellipsoid at the spatial position on the top table using the generated three-dimensional model.

7. The X-ray diagnostic apparatus according to claim 4, wherein the processing circuitry is further configured to generate the three-dimensional model, based on patient characteristic information that represents characteristics of the patient, and based on the system position information.

8. The X-ray diagnostic apparatus according to claim 4, wherein the system position information includes patient position information that represents a position of the patient, and
the processing circuitry is further configured to identify the irradiation region where the patient is irradiated, by the three-dimensional model that moves along with a change in the patient position information and the irradiation position information that are included in the system position information, based on the patient position information and the irradiation position information, and adjust the X-ray irradiation range.

9. The X-ray diagnostic apparatus according to claim 4, wherein the processing circuitry is further configured to generate a projection image of the three-dimensional model along with the change in the system position information, and identify an outer frame of the vascular region of the projection image as the irradiation region where the patient is irradiated, and
control the X-ray diaphragm to adjust the X-ray irradiation range so as to irradiate the identified irradiation region with the X-rays.

10. The X-ray diagnostic apparatus according to claim 4, wherein the processing circuitry is further configured to generate a projection image of the three-dimensional model along with the change in the system position information, and identify the irradiation region where the patient is irradiated, from the projection image, and attenuate the X-rays using a compensation filter.

11. The X-ray diagnostic apparatus according to claim 9, wherein the processing circuitry is further configured to
detect a distal end of a vascular insertion device in the three-dimensional model,
detect the distal end of the vascular insertion device in the irradiation region, project a position of the distal end of the vascular insertion device onto the projection image, compare the vascular insertion device in the projection image with the vascular insertion device in a live image during irradiation of the X-rays, and, when a deviation in the position is detected, correct the position of the three-dimensional model, and
adjust the X-ray irradiation range so as to irradiate the irradiation region with the X-rays in a state where the vascular insertion device in the live image during X-ray irradiation and the vascular insertion device in the projection image coincide with each other.

12. The X-ray diagnostic apparatus according to claim 1, wherein the system position information includes at least any one of an arm angle, a SID, and a FOV in the irradiation position information.

13. The X-ray diagnostic apparatus according to claim 1, wherein the system position information includes at least any one of a height of a catheter table, a longitudinal tilt, and a lateral tilt in the patient position information.

14. The X-ray diagnostic apparatus according to claim 1, wherein the processing circuitry is further configured to identify the three-dimensional region from the X-ray images varying with a change in heartbeat and respiration.

15. The X-ray diagnostic apparatus according to claim 1, wherein, the processing circuitry is further configured to
store the identified three-dimensional region of the patient in a storage medium,
retrieve the three-dimensional region of the patient from the storage medium,
align the retrieved three-dimensional region of the patient with the patient based on an X-ray image of the patient, and
adjust an X-ray irradiation range where the patient is irradiated by controlling an X-ray diaphragm, or attenuate an X-ray irradiation to a region other than the X-ray irradiation range by controlling a filter.

16. A method of adjusting an irradiation range of an X-ray diagnostic apparatus that reads a program from a memory and executes the program using processing circuitry, the method comprising:
identifying two-dimensional vascular regions in corresponding X-ray images taken in at least two directions,
correcting a size of each of the vascular regions on corresponding each of the X-ray images so as to have a corresponding size at a spatial position on a top table on which a patient is mounted, identifying a three-dimensional region of the patient at the spatial position on the top table based on the corrected vascular regions, and along with a change in system position information, adjusting an X-ray irradiation range by controlling an X-ray diaphragm, or attenuating an X-ray irradiation to a region other than the identified three-dimensional region by controlling a filter, based on the identified three-dimensional region and based on the system position information, which includes irradiation position information indicating where the patient is irradiated.

* * * * *